US008894609B2

(12) United States Patent
Gobbi Frattini

(10) Patent No.: US 8,894,609 B2
(45) Date of Patent: Nov. 25, 2014

(54) BAG FOR MIXABLE LIQUID SOLUTIONS

(71) Applicant: Ditta Paolo Giuseppe GOBBI FRATTINI, Sondalo (IT)

(72) Inventor: Paolo Giuseppe Gobbi Frattini, Sondalo (IT)

(73) Assignee: Ditta Paola Giuseppe Gobbi Frattini, Sondalo SO (IT)

( * ) Notice: Subject to any disclaimer, the term of this patent is extended or adjusted under 35 U.S.C. 154(b) by 0 days.

(21) Appl. No.: 13/864,529

(22) Filed: Apr. 17, 2013

(65) Prior Publication Data

US 2013/0281923 A1 Oct. 24, 2013

(30) Foreign Application Priority Data

Apr. 18, 2012 (IT) .............................. MI2012A0643

(51) Int. Cl.

*A61M 37/00* (2006.01)
*A61J 1/10* (2006.01)
*A61J 1/20* (2006.01)
*A61J 1/14* (2006.01)

(52) U.S. Cl.

CPC *A61J 1/2089* (2013.01); *A61J 1/10* (2013.01); *A61J 2001/1487* (2013.01); *A61J 1/1462* (2013.01); *A61J 2001/1481* (2013.01); *A61J 1/1406* (2013.01)

USPC .............................. 604/87; 604/408; 604/411

(58) Field of Classification Search

CPC ............. A61J 1/10; A61J 1/20; A61J 1/1475; A61J 1/2089; A61J 1/2093; A61J 1/2096; A61M 5/1409

USPC ........ 216/219; 604/30, 85, 87, 403, 408, 410, 604/411, 416

See application file for complete search history.

(56) References Cited

U.S. PATENT DOCUMENTS

| | | | | |
|---|---|---|---|---|
| 4,403,992 | A * | 9/1983 | Bertellini et al. | 604/410 |
| 4,606,734 | A * | 8/1986 | Larkin et al. | 604/84 |
| 5,817,083 | A | 10/1998 | Shemesh | |
| 5,971,972 | A * | 10/1999 | Rosenbaum | 604/411 |
| 6,491,679 | B1 * | 12/2002 | Okamoto et al. | 604/410 |
| 2002/0023851 | A1 | 2/2002 | Muller | |
| 2004/0116891 | A1 * | 6/2004 | Curutcharry | 604/403 |
| 2004/0241041 | A1 * | 12/2004 | Woodworth et al. | 422/22 |
| 2008/0234654 | A1 * | 9/2008 | McCarthy et al. | 604/416 |
| 2009/0030396 | A1 | 1/2009 | Ferris | |
| 2009/0264854 | A1 * | 10/2009 | Jensen et al. | 604/416 |
| 2010/0133203 | A1 * | 6/2010 | Walker et al. | 210/748.11 |
| 2011/0144613 | A1 * | 6/2011 | Pepper et al. | 604/410 |
| 2013/0123739 | A1 * | 5/2013 | Yoshikawa | 604/408 |

FOREIGN PATENT DOCUMENTS

WO 99/59522 11/1999

* cited by examiner

*Primary Examiner* — Nicholas Lucchesi
*Assistant Examiner* — Gerald Landry, II
(74) *Attorney, Agent, or Firm* — Jacobson Holman Hershkovitz, PLLC.

(57) ABSTRACT

A flexible bag (1) that is partially filled with a basic liquid solution (21) has a first end closure (3) from which a mixing tube (7) extends that is provided with a frangible closure cap (8) and a terminal (9) that is suitable for the connection of a container (22) of active substance (23) to be mixed with the basic liquid solution (21) and a second end closure (5) from which two dispensing tubes (12, 13) extend that are provided with respective frangible closure caps (14, 15). A first dispensing tube (12) has a terminal (18) of the press type and a second dispensing tube (13) has a terminal (19) of the screw type (FIG. 1).

4 Claims, 5 Drawing Sheets

BAG FOR MIXABLE LIQUID SOLUTIONS

BACKGROUND OF THE INVENTION

The present invention relates to a bag for liquid solutions that are mixable with active substances available in a separate form, in particular in powder or gel, for forming liquid medicinal or liquid substances that are administrable to patients through internal instillation.

BRIEF SUMMARY OF THE INVENTION

In hospital environments, there is often a need to administer to patients, by internal instillation, medicinal and nutritional substances of different kinds that are made available separately, in particular in powder or gel, inside suitable sealed bottles.

In order to make the active substances suitable for instillation in liquid form it is necessary to form a mixture that comprises, in addition to the active substance, a basic liquid solution that acts as a solvent.

This basic liquid solution is usually available inside a flexible bag, from the base of which there extend a mixing tube with a connecting terminal for a container of active substance and a dispensing tube with a connecting terminal for a catheter, both provided with respective frangible caps and with possible closing clamps.

A connection for a syringe for dosing the quantity of active substance to be mixed with the basic liquid solution is sometimes associated with the mixing tube.

The dispensing tube can be provided with a press-fit type terminal or with a screw-type terminal for the connection and fixing thereof to a catheter or the like that is suitable for administrating the mixed substance inside the body of the patient. This entails the availability, inside the treatment facility, of two distinct sets of bags, one with a dispensing tube that is couplable with a press-fit coupling, the other that is couplable with a screw fit coupling, with the consequent need of double availability of storage space and an equally double financial investment.

The object of the present invention is to overcome this drawback by making a bag that is suitable for both the types of aforementioned coupling.

This object is achieved with a flexible bag that is partially filled with a basic liquid solution and has a first end closure from which a mixing tube extends that is provided with a frangible closure cap and with a terminal that is suitable for the connection of a container of active substance to be mixed with the basic liquid solution and a second end closure from which two dispensing tubes provided with respective frangible closure caps extend, a first dispensing tube having a press-fit type terminal and a second dispensing tube having a screw-type terminal.

It is clear that the bag according to the invention completely overcomes the drawback exposed above because the two dispensing tubes of different type make the bag suitable for connection to both a press-fit type catheter and to a screw-type catheter.

It should be further noted that, as the mixing tube extends from the opposite end of the bag to the two dispensing tubes, once mixing has been performed after connection of the container of active substance and breaking of the frangible closure cap it is sufficient to connect the bag in an upturned position in order for the formed mixture to remain by gravity inside the bag even in the absence of a closing clamp of the mixing tube. The force of gravity will then enable the mixture to be dispensed through the appropriate dispensing tube once the dispensing tube has been connected to the destination catheter and once the corresponding frangible cap has been broken.

BRIEF DESCRIPTION OF THE DRAWINGS

The constructional features and the operating procedures of the bag according to the invention will become clear from the following detailed description of a possible embodiment thereof shown by way of non limiting example in the attached drawings, in which.

DETAILED DESCRIPTION OF THE INVENTION

Figure 1:
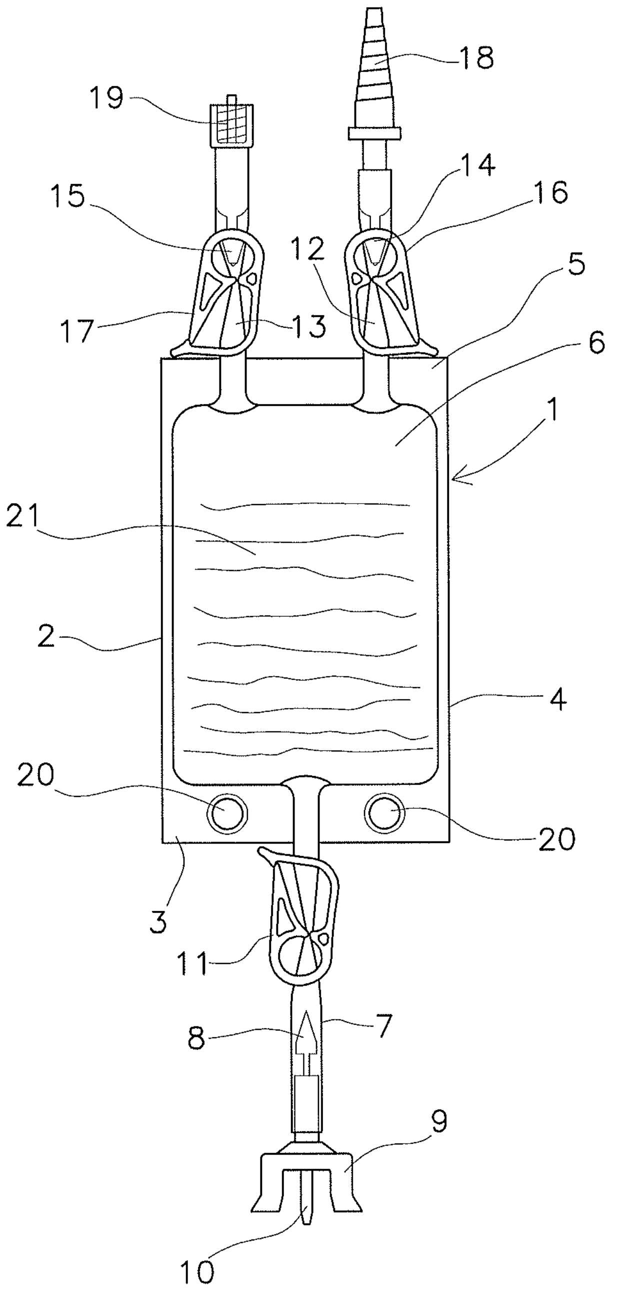
FIG. 1 shows a bag according to the present invention in a non-operating condition.

In FIG. 1, a bag 1 of transparent flexible plastic material is shown that is closed on four sides 2, 3, 4 and 5 to form a body in the shape of a quadrilateral with an internal cavity 6.

A flexible mixing pipe 7 that is closed by a frangible cap 8 (of per se known type) and terminates in a hooking head 9 provided with a hollow perforating tip 10 extends from the cavity 6 through the side 3 of the bag to the outside. A clamp 11 that is openable and closable by manual pressure is interposed between the side 3 of the bag and the frangible cap 8.

Two flexible dispensing tubes 12 and 13 that are closed by respective frangible caps 14 and 15 and are further provided with respective clamps 16 and 17 that are openable and closable by manual pressure extend from the cavity 6 through the opposite side 5 of the bag 1 (in the opposite direction to the tube 7) to the outside. The dispensing tubes 12 and 13 have respective terminals 18 and 19 that are suitable for coupling, respectively with press-fit type and with screw-type couplings, with catheters that are insertable into the body of a patient.

Two holes 20 are provided in the side 3 of the bag 1 for hooking the bag in a hung condition.

In a non-operating condition, the bag 1 is located as shown in FIG. 1, namely filled with basic liquid solution 21 and with the frangible caps 8, 14 and 15 and the clamps 11, 16 and 17 in the closing position.

Figure 2:
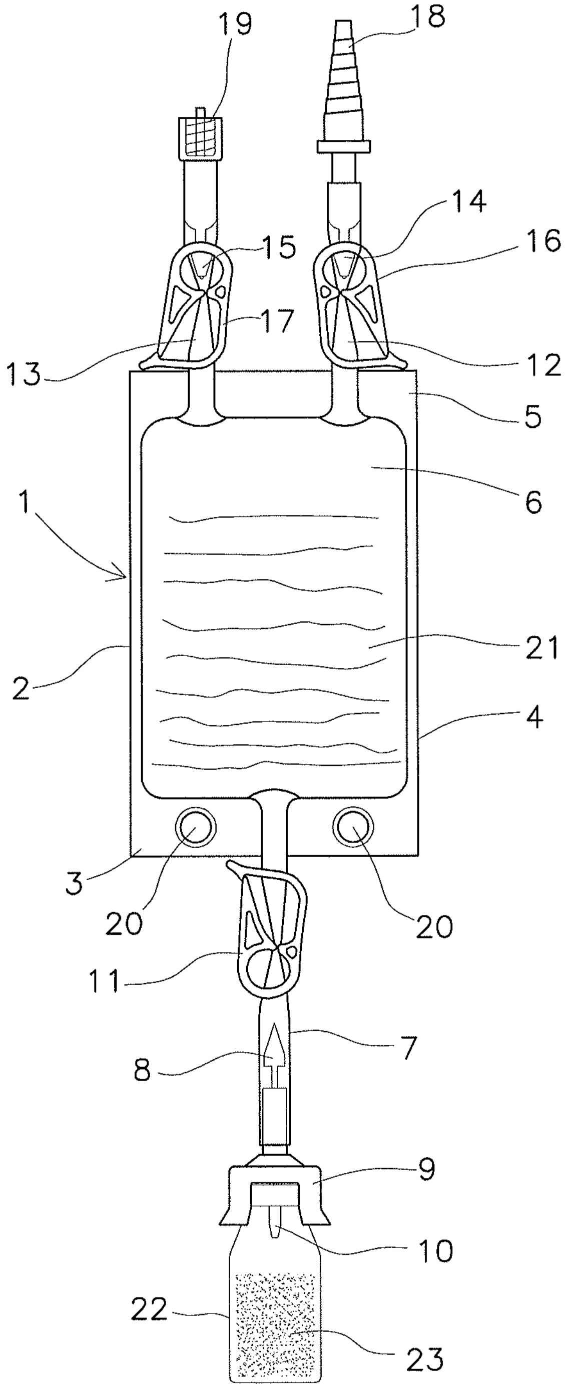
FIG. 2 shows the device in FIG. 1 after hooking and perforation of a bottle with an active powder substance.
Figure 3:
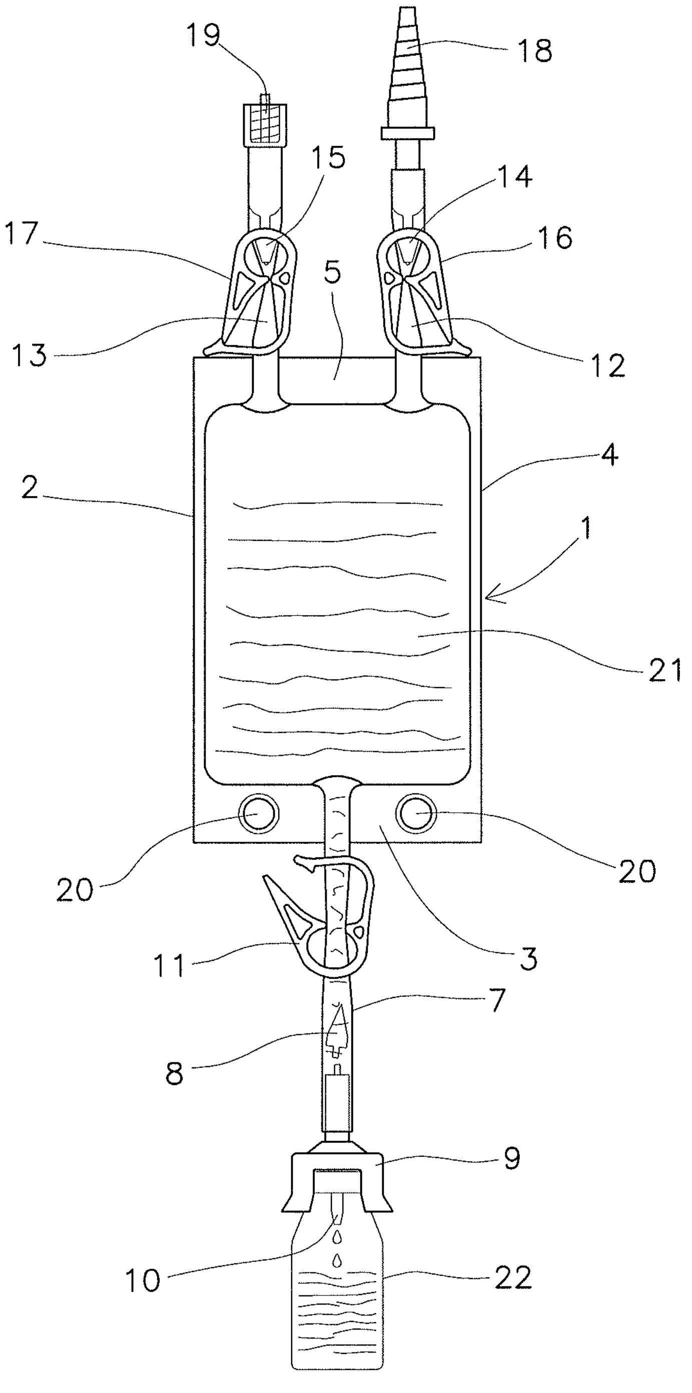
FIG. 3 shows the bag in the transfer step of a quantity of basic solution from the bag to the bottle for the transformation of the active substance into a powder in a liquid mixture.

In order to mix the basic liquid solution with an active substance (medicinal or nutritional, in powder or gel) the head of a bottle 22 must be inserted and hooked in the terminal 9 of the tube 7 and the aforesaid active substance 23, such that the perforation tip 10 passes through the upper closure of the bottle and places the inside of the latter in communication with the tube 7 (FIG. 2). The frangible cap 8 is then broken and the clamp 11 is opened (or vice versa), so that the liquid solution 21 can flow from the cavity 6 of the bag 1 inside the bottle (FIG. 3), pushed by the force of gravity and possibly assisted by the operator squeezing the side of the bag with a hand.

Figure 4:
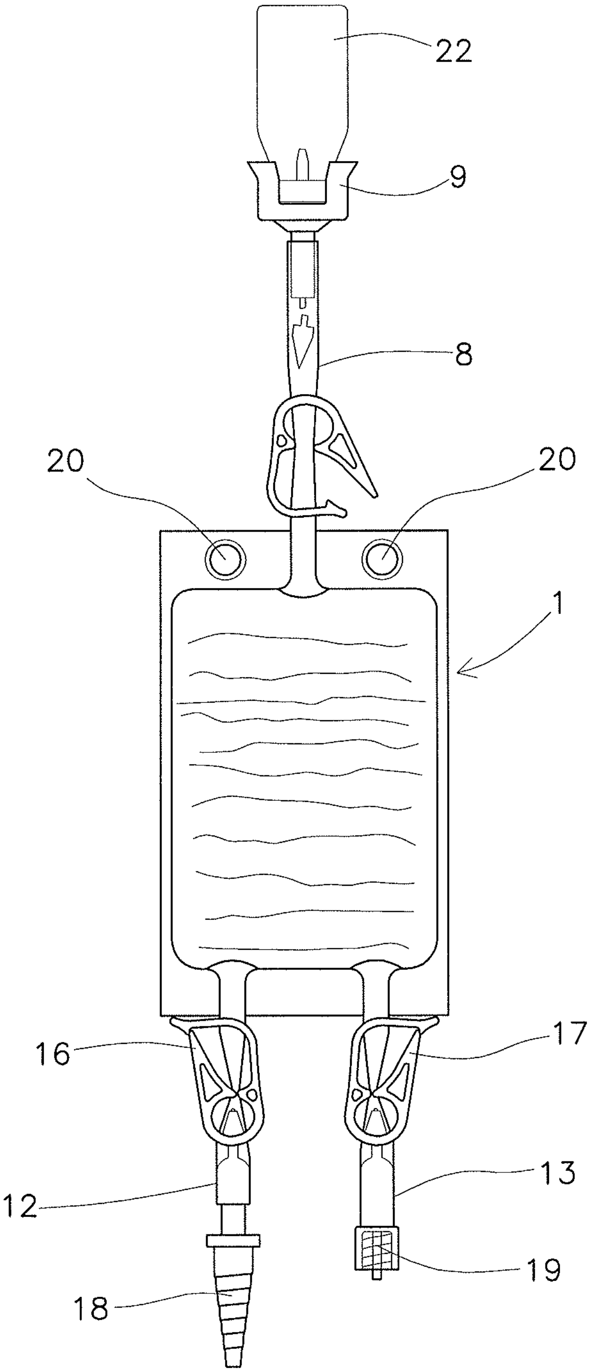
FIG. 4 shows the bag in an upturned position for transferring said liquid mixture from the bottle to the bag.

Once mixing has been performed, and keeping the clamps 16 and 17 closed, the bag is overturned and the mixture can move from the bottle 22 to the internal cavity of the bag, as shown in FIG. 4.

Figure 5:
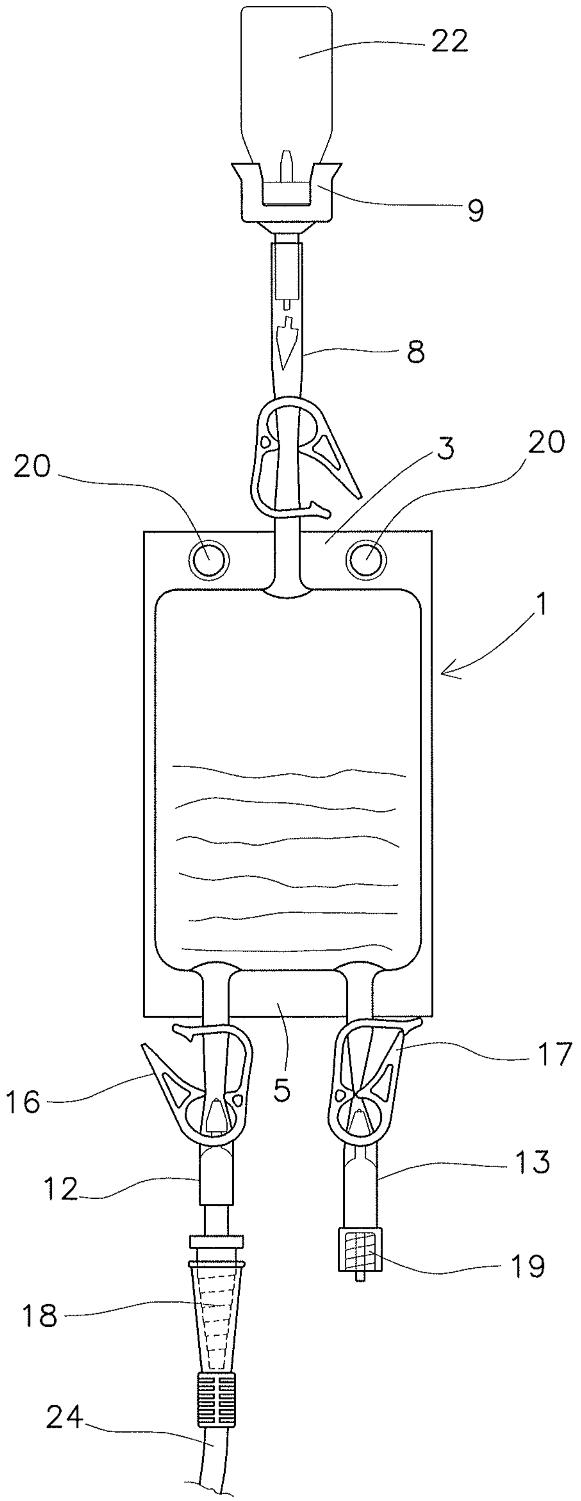
FIG. 5 shows the bag in the position of dispensing the liquid mixture to a catheter for instillation into the body of a patient.

With the bag hanging at one or both holes 20 the mixture that is so formed can be made to flow into the catheter intended for instillation (catheter 24 with press-type coupling in FIG. 5 or another catheter with screw-type coupling alternatively) by using one or the other of the two dispensing tubes 12 and 13 by breaking the relative pressure cap 14 or 15 and opening the corresponding clamp 16 or 17.

It should be noted that hooking the bag at one and/or the other of the two holes 20 makes the presence of the closing clamp 11 of the mixing tube 8 unnecessary.

It should also be noted that by hooking the bag at only one of the holes 20 a tilt of the bag is created that favours the flow of the mixture through the tube below the non-hooked hole.

After instillation has been terminated, the clamp of the tube used for dispensing is closed and the terminal of the tube is detached from the catheter used, taking care to apply a suitable closure cap to the aforesaid terminal.

The invention claimed is:

1. A flexible bag partially filled with a basic liquid solution, the flexible bag having a first closed end from which a mixing tube extends which is provided with an intermediate frangible closure plug, and with a terminal suitable for the connection of a container of active substance to be mixed with the basic liquid solution and a second closed end from which a first dispensing tube and a second dispensing tube provided with respective intermediate frangible closure plugs extend, the first dispensing tube having a press-fit type terminal closure device and the second dispensing tube having a screw type terminal closure device.

2. The flexible bag according to claim 1, wherein said first closed end is provided with holes for the connection of the bag in hanging condition.

3. The flexible bag according to claim 1, wherein each of said dispensing tubes is also provided with a respective closure clamp.

4. The flexible bag according to claim 1, wherein said mixing tube is also provided with a closure clamp.

* * * * *